US011077204B2

(12) United States Patent
Osinga et al.

(10) Patent No.: US 11,077,204 B2
(45) Date of Patent: Aug. 3, 2021

(54) COMPOSITIONS COMPRISING ANTIBODY-DUOCARMYCIN DRUG CONJUGATES

(71) Applicant: Byondis B.V., Nijmegen (NL)

(72) Inventors: Niels Jaap Osinga, Nijmegen (NL); Ernst Johannes Bernardus Van Bockxmeer, Nijmegen (NL)

(73) Assignee: Byondis B.V., Nijmegen (NL)

( * ) Notice: Subject to any disclaimer, the term of this patent is extended or adjusted under 35 U.S.C. 154(b) by 611 days.

(21) Appl. No.: 15/743,413

(22) PCT Filed: Jul. 8, 2016

(86) PCT No.: PCT/EP2016/066347
§ 371 (c)(1),
(2) Date: Jan. 10, 2018

(87) PCT Pub. No.: WO2017/009255
PCT Pub. Date: Jan. 19, 2017

(65) Prior Publication Data
US 2018/0200382 A1    Jul. 19, 2018
US 2019/0216942 A9    Jul. 18, 2019

(30) Foreign Application Priority Data

Jul. 10, 2015   (EP) ..................................... 15176307

(51) Int. Cl.
| | | |
|---|---|---|
| A61K 47/68 | (2017.01) | |
| A61K 47/18 | (2017.01) | |
| A61K 47/26 | (2006.01) | |
| A61K 9/19 | (2006.01) | |
| C07K 16/32 | (2006.01) | |
| A61K 31/4184 | (2006.01) | |
| A61K 39/395 | (2006.01) | |
| C07K 16/28 | (2006.01) | |
| C07K 16/30 | (2006.01) | |

(52) U.S. Cl.
CPC ............ *A61K 47/6809* (2017.08); *A61K 9/19* (2013.01); *A61K 31/4184* (2013.01); *A61K 39/3955* (2013.01); *A61K 47/183* (2013.01); *A61K 47/26* (2013.01); *A61K 47/6803* (2017.08); *A61K 47/6851* (2017.08); *C07K 16/2863* (2013.01); *C07K 16/30* (2013.01); *C07K 16/32* (2013.01); *C07K 2317/24* (2013.01)

(58) Field of Classification Search
CPC ............ A61K 47/6803; A61K 47/6809; A61K 47/6851; A61K 47/183; A61K 47/18; A61K 47/26; A61K 9/19; A61K 31/4184
See application file for complete search history.

(56) References Cited

U.S. PATENT DOCUMENTS

| | | | |
|---|---|---|---|
| 9,421,278 | B2 | 8/2016 | Dokter et al. |
| 9,427,480 | B2 | 8/2016 | Santin et al. |
| 9,629,924 | B2 | 4/2017 | Beusker et al. |
| 2009/0286258 | A1 | 11/2009 | Kaur et al. |
| 2017/0007717 | A1 | 1/2017 | Santin et al. |
| 2017/0274090 | A1 | 9/2017 | Beusker et al. |
| 2017/0333567 | A1 | 11/2017 | Beusker et al. |
| 2018/0140711 | A1 | 5/2018 | Santin et al. |

FOREIGN PATENT DOCUMENTS

| | | |
|---|---|---|
| EP | 1626740 B1 | 8/2014 |
| WO | WO-2004110498 A2 | 12/2004 |
| WO | WO 2009/017394 A1 | 2/2009 |
| WO | WO 2010/062171 A2 | 6/2010 |
| WO | WO-2011133039 A2 | 10/2011 |
| WO | WO-2012162482 A1 | 11/2012 |
| WO | WO-2015075201 A1 | 5/2015 |
| WO | WO-2015104373 A2 | 7/2015 |
| WO | WO-2017009255 A1 | 1/2017 |

OTHER PUBLICATIONS

Debaene, Journal of Analytical Chemistry, 2014, vol. 86, p. 10674-10683 (Year: 2014).*
Moeller et al (Drug Discovery Today, 2008, vol. 5, pp. e89-e94) (Year: 2008).*
Chang et al ('Lyophilized Biologies' in Lyophilized Biologies and Vaccines, 2015, Varshney and Singh, Eds, pp. 93-119) (Year: 2015).*
Harris et al (Drug Development Research, 2004, vol. 61, pp. 137-154) (Year: 2004).*
Nolli et al., "Antibodies against the antibiotics: an overview," Ann Ist Super Sanita 27(1):149-54, Instituto Superiore di Sanita, Italy (1991).
Dokter, W., et al., "Preclinical Profile of the HER2-Targeting ADC SYD983/SYD985: Introduction of a New Duocarmycin-Based Linker-Drug Platform," Molecular Cancer Therapeutics 13(11):2618-2629, American Association for Cancer Research, United States (Nov. 2014).
International Preliminary Report on Patentability for Application No. PCT/EP2016/066347, dated Jan. 16, 2018, 6 pages.
International Search Report and Written Opinion for International Application No. PCT/EP2016/066347, dated Sep. 14, 2016, 9 pages.
NCT02277717, "First-in-human Study With the Antibody-drug Conjugate SYD985 to Evaluate Safety and Efficacy in Cancer Patients," ClinicalTrials.gov archive, accessed at https://clinicaltrials.gov/ct2/show/NCT02277717, accessed on Jun. 19, 2018.
NCT00944905, "Study of MDX-1203 in Subjects With Advanced/Recurrent Clear Cell Renal Cell Carcinoma (ccRCC) or Relapsed/Refractory B-Cell Non-Hodgkin's Lymphoma (B-NHL)," ClinicalTrials.gov archive, accessed at https://clinicaltrials.gov/ct2/show/NCT00944905, accessed on May 22, 2013.

* cited by examiner

*Primary Examiner* — Karen A. Canella
(74) *Attorney, Agent, or Firm* — Sterne, Kessler, Goldstein & Fox P.L.L.C.

(57) ABSTRACT

The present invention relates to lyophilized compositions comprising antibody-duocarmycin drug conjugates.

25 Claims, 4 Drawing Sheets

Figure 4

COMPOSITIONS COMPRISING ANTIBODY-DUOCARMYCIN DRUG CONJUGATES

FIELD OF THE PRESENT INVENTION

The present invention relates to lyophilized compositions comprising antibody-duocarmycin drug conjugates and reconstituted aqueous solutions thereof.

BACKGROUND OF THE PRESENT INVENTION

Duocarmycins are toxins isolated from *Streptomyces* sp. in 1988. These DNA binding and alkylating agents exhibit potent cytotoxicity in vitro. However, their application in cancer treatment is limited because, in vivo, they have unfavourable side effects resulting in a small therapeutic index.

The therapeutic index of anti-tumour agents can be improved by incorporating them in an antibody-drug conjugate (ADC). An ADC is obtained by conjugating a drug, via a cleavable or non-cleavable linker (linker drug), to an antibody.

Currently, two ADCs are marketed, i.e., brentuximab vedotin and trastuzumab emtansine, and over 30 ADCs are in various phases of clinical development. The developments regarding ADCs prompted renewed interest in developing duocarmycins and particularly duocarmycin derivatives as drugs in ADCs. These ADCs are referred to as antibody-duocarmycin drug conjugates or duocarmycin-derived ADCs in the present application.

Two duocarmycin-derived ADCs, i.e., SYD985 (NCT02277717 (2014); Sponsor: Synthon Biopharmaceuticals) and MDX-1203 (NCT00944905 (2009); Sponsor: Bristol-Myers Squibb), are currently in clinical development.

Compared to naked (monoclonal) antibodies, ADCs have different physicochemical properties; hence, conventional pharmaceutical formulations suitable for monoclonal antibodies are not equally suitable for ADCs. Most linker drugs, in particular those containing duocarmycin derivatives, have a low solubility in water. When these linker drugs are conjugated to antibodies, the resulting conjugate has an increased hydrophobicity as compared to the naked antibody, decreasing the colloidal stability of the ADC in an aqueous solution. The hydrophobicity increase upon conjugation of a linker drug is pronounced as compared to the variation in hydrophobicity between different antibodies. This poses difficulties for pharmaceutical formulation development. Not only the type of linker drug, but also the number of linker drugs per antibody (Drug-to-Antibody Ratio, DAR) and the site(s) of conjugation of the linker drug to the antibody influence the physicochemical properties of the ADC. As compared to a naked antibody, the corresponding ADC tends to aggregate more easily. Furthermore, the higher the DAR, the higher is the tendency for aggregation in solution.

Additionally, to ensure the chemical stability of the linker drug, especially in the case of a cleavable linker, the ADC formulation has to comply with requirements different from those necessary for the stability of the naked antibody per se. As each linker drug has a different chemical stability and hydrophobicity, each ADC is unique and requires a dedicated, tailored composition.

In order to have sufficient shelf life, protein-derived drugs are often marketed as a lyophilized powder for reconstitution with water. To obtain a lyophilized powder, a lyophilization or freeze-drying process is employed. This lyophilisation process has three stages, i.e., freezing, primary drying, and secondary drying. Primary drying conditions are chosen in such a way that the product temperature remains below the collapse temperature of the composition to prevent physical collapse of the cake. The collapse temperature of the composition can be determined using Freeze-Dry Microscopy. Secondary drying is performed below the glass transition temperature (Tg) of the composition, which temperature is usually determined by differential scanning calorimetry (DSC).

Before the lyophilisation process can commence, the active pharmaceutical ingredient needs to be provided in a suitable formulation. In the case of an ADC formulation, the purification formulation typically is exchanged with a formulation suitable for lyophilisation, i.e., to provide a pre-lyophilisation solution. The pre-lyophilisation solution needs to fulfil several demands, i.e., it should solubilise the ADC completely; in the pre-lyophilisation solution the ADC should be colloidally and chemically stable for a certain period of time at various conditions, e.g. temperature, generally occurring during lyophilisation; the process time should be acceptable; and the ADC should be stable in the resulting lyophilized composition, typically referred to as lyophilized powder or cake. This cake should have an acceptable appearance. Additionally, the lyophilized composition should be easily reconstitutable.

Usually, lyophilized protein formulations contain a buffering agent, a lyoprotectant and, optionally, a surfactant or a bulking agent or both. The lyophilized powder typically is stored in a vial and is reconstituted with bacteriostatic or sterile water for injection.

The ADCs that are currently marketed are available as a lyophilized powder. However, these ADCs contain toxins, viz. a maytansinoid (e.g. DM1) or an auristatin (e.g. monomethyl auristatin E), that are less hydrophobic than the duocarmycin-derived toxins currently being investigated as drugs in ADCs and these ADCs have different DARs than the duocarmycin-derived ADCs used in the formulations of the present invention. The physico-chemical properties of these and other maytansinoid or auristatin ADCs are different from those of the duocarmycin-derived ADCs used in the formulations of the present invention and require different formulations.

For instance, the composition of T-DM1, i.e. trastuzumab conjugated via a non-cleavable linker to emtansine, having a DAR of 3.5 (Kadcyla®) upon reconstitution, is 20 mg/ml T-DM1, 10 mM sodium succinate, 6% (w/v) sucrose, 0.02% (w/v) polysorbate 20, pH 5.0.

WO2004/110498 relates to liquid and lyophilized compositions of an antibody coupled to a maytansinoid and discloses inter alia lyophilized compositions of huN901-DM1 ADCs (1-5 mg/ml), having a DAR of about 4, of a solution comprising 10 mM sodium succinate, 0.01% (w/v) polysorbate 20, 0.5% (w/v) sucrose (i.e. over 10 times less than the sucrose amount in the commercial formulation of Kadcyla®), 250 mM glycine and pH 5.5. Example 6 of WO2004/110498 teaches that compositions comprising 1 mg/ml huN901:DM1 ADC, 10 mM sodium succinate in combination with 0.01% polysorbate 20 and 250 mM glycine gives better stability than the combination of 10 mM sodium citrate, 0.01% polysorbate 20 and 250 mM glycine. Formulations without polysorbate are not stable. Example 7 of WO2004/110498 shows that a similar formulation comprising 5 mg/ml huN901-DM1, resulting in a 5 times lower ADC-to-sucrose ratio than the preferred formulation of Example 6, is stable as well. WO2004/110498 solely discloses lyophilized formulations of huN901:DM1 ADC that comprise 250 mM glycine, which not only acts as a bulking agent, but has cryo- or lyoprotective properties as well. Therefore the disclosed formulations have a high lyoprotectant/ADC molar ratio.

The commercial formulation of Adcetris® has the composition after reconstitution of 5 mg/ml brentuximab vedotin, a monomethyl auristatin E (MMAE) conjugate to a chimeric monoclonal antibody of the IgG1 type (DAR of about 8), 5.6 mg/ml sodium citrate, 0.21 mg/ml citric acid monohydrate, 70 mg/ml trehalose dihydrate, 0.2 mg/ml polysorbate 80 and has a pH of 6.6.

WO2015/075201 discloses surfactant-free lyophilized formulations comprising an ADC wherein an anti-TF IgG1 antibody is conjugated to MMAE via a valine-citrulline linker, similar to the linker drug of Adcetris®. This ADC has a DAR of 4 (p. 35, 1. 6). Example 7 on p. 55 teaches that compositions containing 10 mg/ml ADC, 30 mM histidine, and 150 mM or 250 mM sucrose show severe shrinkage (inferior cake quality/appearance) starting from a fill volume of 4 ml in a 10 ml vial, which makes these formulations unsuitable for commercial production. It also teaches that the presence of a bulking agent (mannitol is present in the pre-lyophilisation solution in a relatively high amount of at least 3% w/v) is necessary for good cake quality. Example 8 discloses that a ratio of sucrose to ADC of 1,337 to 1 is preferred (i.e. Formulation B), whereas Example 12 shows there is no difference in stability between formulations having a sucrose to ADC ratio of 2,676 to 1 and formulations having a sucrose to ADC ratio of 446 to 1.

Several liquid formulations in relation to duocarmycin-derived ADCs have been disclosed, e.g. in WO 2012/162482 (p. 35, 1. 16-17), WO 2011/133039 (p. 218, 1. 24), and on p. 2 of in the supplementary information of DOKTER, W et al. Preclinical Profile of the HER2-Targeting ADC SYD983/SYD985 Mol. Cancer Ther.; 13(11) November 2014; 2618-2629. The formulation of WO2012/162482 is not suitable for lyophilisation, as it contains a high amount of sodium chloride which can reduce the collapse temperature of the composition to impractically low values. WO 2011/133039 discloses a series of novel analogues of the DNA alkylating agent CC-1065 and HER2-targeting ADCs formulated in the commercial Herceptin® (trastuzumab) formulation comprising 4.2 mM histidine, 19.1 mg/ml trehalose dihydrate, and a polysorbate, having a pH of 6. In DOKTER, W et al., a formulation comprising histidine, 30 mg/ml trehalose dihydrate, and a polysorbate, having a pH of 6 was used for the HER2-targeting duocarmycin-derived ADC SYD983.

However, no lyophilized formulations comprising duocarmycin-derived ADCs have been disclosed in the prior art.

The liquid formulations disclosed in WO 2011/133039 and DOKTER, W et al. are unsuitable for lyophilization, because the stability of a duocarmycin-derived ADC in the formulation and the quality of the lyophilized cake is inferior in formulations that have a relatively low molar ratio of lyoprotectant to ADC. In view of the lack of suitable pharmaceutical formulations for duocarmycin-derived ADCs in the state of the art, there is a clear need for lyophilized compositions comprising duocarmycin-derived ADCs having a acceptable cake appearance and which can be prepared with a lyophilization process having an acceptable lyophilization time, and in which the duocarmycin-derived ADCs are acceptably stable.

BRIEF DESCRIPTION OF THE PRESENT INVENTION

The present invention relates to lyophilized compositions comprising antibody-duocarmycin drug conjugates of formulae (I) or (II) and corresponding reconstituted aqueous solutions thereof.

DETAILED DESCRIPTION OF THE PRESENT INVENTION

The present invention provides a lyophilized composition comprising an antibody-drug conjugate (ADC) of formula (I), a buffering agent, a lyoprotectant and a surfactant wherein the molar ratio of lyoprotectant to antibody-drug conjugate is 1,400-3,200 to 1.

In the ADCs of formula (I) and (II) (see below) the linker drug is conjugated to two or more antibody cysteine residues to give an ADC having an average drug to antibody ratio (DAR) of 2-3. Preferably, the ADC has an average DAR of 2.5-3.0, more preferably an average DAR of 2.6-2.9.

The ADCs of formulae (I) and (II) to be used in the composition in accordance with the present invention have the linker drug conjugated to the antibody through the S-atom of a cysteine residue, i.e., they are cysteine-linked antibody-drug conjugates. Typically, the cysteine residue is a natural cysteine residue which is present in the heavy and/or light chain of the (monoclonal) antibody (mAb) and forms interchain disulfide bonds. Antibodies of different antibody classes contain different numbers of interchain disulfide bonds. For example, IgG1 antibodies typically have four interchain disulfide bonds—all four located in the hinge region—and after (partial) reduction of the disulfide bonds the linker drug is randomly attached to the free thiol groups.

Antibody-drug conjugates of formulae (I) and (II) for use in accordance with the present invention can be obtained according to methods and procedures that are well known to a person skilled in the art. Conjugation through interchain disulfide bonds can occur after complete or partial reduction of said disulfide bonds. Suitable methods for preparing such compounds can be found in the description and examples of WO 2011/133039 as well as in the supplementary information of DOKTER, W et al. in Mol. Cancer Ther.; 13(11) November 2014; 2618-2629 (disclosing HIC purification of the ADC SYD983 to give SYD985). In particular, Example 15 of WO 2011/133039 describes the partial reduction of trastuzumab to generate two free thiol groups per mAb and conjugation with a number of linker drugs to ADCs having an average DAR of approximately 2. It is easily understood by those skilled in the art how to obtain ADCs having an average DAR of 2-3 in accordance with the present invention.

In a typical embodiment of the composition of the present invention, the antibody-drug conjugate (ADC) is present in the composition in an amount providing a concentration of 1-30 mg/ml when reconstituted with water. Preferably, the amount is providing a concentration of 2-20 mg/ml, more preferably 5-15 mg/ml, most preferably about 10 mg/ml when reconstituted with water.

The monoclonal antibody (mAb) used for conjugation with a linker drug and for inclusion into a composition in accordance with the present invention can be an IgA, IgD, IgE, IgG or IgM antibody. The antibody can have κ (kappa) light chains or λ (lambda) light chains. The IgG antibody can be an IgG1, IgG2, IgG3 or IgG4 antibody. Preferably, the antibody binds to a(n) antigen target that is expressed in or on the cell membrane (e.g., on the cell surface) of a tumour cell, more preferably, the antibody is internalised by the cell after binding to the (antigen) target, after which the duocarmycin drug is released intracellularly. Preferably, the antibody is an IgG antibody, more preferably an IgG1 antibody, most preferably an IgG1 antibody having κ light chains. Preferably, the IgG antibody carries a native glycoside/carbohydrate moiety attached at N297 of the heavy chain of the antibody.

Suitable antibodies include an anti-annexin A1 antibody, an anti-CD19 antibody, an anti-CD22 antibody, an anti-CD30 antibody, an anti-CD33 antibody, an anti-CD37 antibody, an anti-CD38 antibody, an anti-CD44 antibody, an anti-CD47 antibody, an anti-CD56 antibody, an anti-CD70 antibody, an anti-CD74 antibody, an anti-CD79 antibody, an anti-CD115 antibody, an anti-CD123 antibody, an anti-CD138 antibody, an anti-CD203c antibody, an anti-CD303 antibody, an anti-CEACAM antibody, an anti-CLL-1 antibody, an anti-c-MET (or anti-HGFR) antibody, an anti-Cripto antibody, an anti-DLL3 antibody, an anti-EGFR antibody, an anti-EPCAM antibody, an anti-EphA2 antibody, an anti-EphB3 antibody, an anti-ETBR antibody, an anti-FcRL5 antibody, an anti-FOLR1 antibody, an anti-GCC antibody, an anti-GPNMB antibody, an anti-HER2 antibody, an anti-HMW-MAA antibody, an anti-integrin antibody, an anti-Lewis A like carbohydrate antibody, an anti-Lewis Y antibody, an anti-LIV1 antibody, an anti-mesothelin antibody, an anti-MN antibody, an anti-MUC1 antibody, an anti-MUC16 antibody, an anti-NaPi2b antibody, an anti-Nectin-4 antibody, an anti-PSMA antibody, an anti-SIRPα antibody, an anti-SLC44A4 antibody, an anti-STEAP-1 antibody, an anti-5T4 (or anti-TPBG, trophoblast glycoprotein) antibody, an anti-Tag72 antibody, an anti-TF (or anti-tissue factor) antibody, an anti-TROP2 antibody, and an anti-VLA antibody.

Preferably, the antibody is an anti-annexin A1 antibody, an anti-HER2 antibody, an anti-CD115 antibody, an anti-CD123 antibody, an anti-CLL-1 antibody, an anti-c-MET antibody, an anti-MUC1 antibody, an anti-PSMA antibody, an anti-5T4 antibody or an anti-TF antibody. More preferably, the antibody is an anti-HER2 antibody, an anti-PSMA antibody or an anti-5T4 antibody. Even more preferred is an anti-HER2 antibody, in particular trastuzumab or a biosimilar thereof.

The antibody to be used in accordance with the present invention is a monoclonal antibody (mAb) and can be a chimeric, humanized or human mAb. Preferably, in accordance with the present invention a humanized or human mAb is used, more preferably a humanized or human IgG antibody, most preferably a humanized or human IgG1 mAb. Preferably, said antibody has κ (kappa) light chains, i.e., a humanized or human IgG1-κ antibody.

The lyoprotectant to be used in the composition in accordance with the present invention can be any excipient which, when combined with the ADC, significantly prevents or reduces chemical and/or physical instability of the ADC upon lyophilization and subsequent storage.

Exemplary lyoprotectants include sugars such as reducing or non-reducing saccharides; amino acids, such as glycine, arginine, proline, lysine, alanine; a methylamine; a lyotropic salt; a polyol such as trihydric or higher sugar alcohols, e.g. glycerin, erythritol, glycerol, arabitol, xylitol, sorbitol, and mannitol; propylene glycol; polyethylene glycol, polymers such as polyvinyl pyrrolidine, polyvinyl alcohol, or polydextran, The preferred lyoprotectant is a non-reducing saccharide, e.g. disaccharides such as trehalose, isotrehaloses, sucrose and isosucroses; trisaccharides, such as melezitose, gentianose, raffinose, erlose and umbelli-ferose; tetrasaccharides, such as stachyose and lychnose; and pentasaccharides, such as verbascose. The lyoprotectant to be used in accordance with the composition of the present invention preferably is trehalose or sucrose, or a mixture thereof, most preferably trehalose. Typically, trehalose dihydrate is used for preparing a composition in accordance with the present invention.

The molar ratio of lyoprotectant to ADC to be used in the composition in accordance with the present invention is 1,400-3,200 to 1. Preferably, a molar ratio of 1,400-3,000 to 1, more preferably 1,400-2,500 to 1, even more preferably 1,400-2,000 to 1, still more preferably 1,400-1,800 to 1, is used. Most preferably, a lyoprotectant to ADC molar ratio of 1,500-1,700 to 1 is used.

The present inventors found that the stability of duocarmycin-derived ADCs was optimal above a molar ratio of lyoprotectant to ADC of 1,400 to 1. The stability and cake appearance of such lyophilized compositions was found to be improved compared to compositions having a molar ratio below 1,400 to 1. The lyoprotectant to ADC molar ratios of the prior art compositions disclosed in WO 2012/162482, i.e., about 350 to 1, and in WO 2011/133039 and DOKTER, W et al. in Mol. Cancer Ther.; 13(11) November 2014; 2618-2629, i.e., 800 to 1, are well below 1,400 to 1. Compositions comprising duocarmycin-derived ADCs having a molar ratio of lyoprotectant to ADC of lower than 1,400 to 1 showed an inferior cake appearance, while placebo compositions, i.e. compositions without a duocarmycin-derived ADC, with a similar ratio showed a acceptable cake appearance. Moreover, the stability of compositions comprising duocarmycin-derived ADCs having a molar ratio of lyoprotectant to ADC of lower than 1,400 to 1 was inferior as well. However, the molar ratio of lyoprotectant to ADC should not be overly high, as the lyophilisation process of compositions having a molar ratio of lyoprotectant to ADC of over 3,200 to 1 was found to be unacceptably time consuming. A long lyophilisation process time causes operational risks, such as degradation of the ADC during the process, and makes the process unsuitable for commercial production.

The buffering agent to be used in the composition in accordance with the present invention may be any buffering agent that does not have a major pH change during freezing. Suitable buffering agents include tris(hydroxymethyl)methylamine, 4-2-hydroxyethyl-1-piperazine-ethanesulfonic acid, succinate, citrate, and histidine. Preferred buffering agents are histidine, citrate, and succinate. More preferred buffering agents are histidine and succinate. The most preferred buffering agent is histidine.

In the composition of the present invention, the buffering agent is present in a concentration of 2.5-25 mM when reconstituted with water, preferably in a concentration of 3.0-10 mM. The most preferred concentration of the buffering agent is about 5 mM, as it was observed that the stability of duocarmycin-derived ADCs in aqueous solution was optimal at that concentration.

The composition according to the present invention typically provides an aqueous solution having a pH of 5.3-6.0 when reconstituted with water. Preferably, the pH is 5.5-5.8. Most preferably, the pH is about 5.7. In the preferred pH ranges, a compromise is reached between the stability of the antibody and the chemical stability of the linker drug, resulting in an optimal stability of the duocarmycin-derived ADC.

The surfactant to be used in the composition in accordance with the present invention preferably is a non-ionic surfactant. Suitable surfactants include alkyl glycosides, poloxamers, and polysorbates. Preferred surfactants are polysorbates, such as polysorbate 20 and polysorbate 80. The most preferred surfactant is polysorbate 20.

The amount of surfactant to be present in the composition of the present invention is such that it reduces aggregation of the ADC in aqueous solution and minimizes the formation of (high molecular weight) particulates when reconstituted with water. The surfactant may be present in an amount providing a concentration of 0.001-0.5% mass/volume (m/v) when reconstituted with water, preferably 0.005-0.05% (m/v), more preferably 0.005-0.02% (m/v). Most preferred is an amount of about 0.01% (m/v).

In a preferred embodiment of the present invention, the lyophilized composition comprises an antibody-drug conjugate of formula (II), histidine, trehalose, and polysorbate wherein the molar ratio of trehalose to ADC is 1,500-1,700 to 1, and, when reconstituted with water, the ADC of formula (II) is present in an amount of 5-15 mg/ml, the histidine concentration is 3.0-10 mM, the amount of polysorbate is 0.005-0.02% (m/v), and the pH is 5.5-5.8.

In a more preferred embodiment of the present invention, the lyophilized composition comprises an ADC of formula (II), histidine, trehalose, and polysorbate 20, wherein the molar ratio of trehalose to ADC is about 1,605 to 1, and when reconstituted with water, the ADC of formula (II) is present in an amount of about 10 mg/ml, the concentration of histidine is about 5 mM, the amount of polysorbate 20 is about 0.01% (m/v), and the pH is 5.5-5.8.

In an even more preferred embodiment of the present invention, the lyophilized composition comprises an ADC of formula (II), histidine, trehalose, and polysorbate 20, wherein the molar ratio of trehalose to ADC is about 1,605 to 1, and when reconstituted with water, the ADC of formula (II) is present in an amount of about 10 mg/ml, the concentration of histidine is about 5 mM, the amount of polysorbate 20 is about 0.01% (m/v), and the pH is about 5.7.

In a most preferred embodiment of the present invention, the lyophilized composition consists of or consists essentially of an ADC of formula (II), histidine, trehalose, and polysorbate 20, wherein the molar ratio of trehalose to ADC is about 1,605 to 1, and when reconstituted with water, the ADC of formula (II) is present in an amount of about 10 mg/ml, the concentration of histidine is about 5 mM, the amount of polysorbate 20 is about 0.01% (m/v), and the pH is about 5.7.

The compound of formula (II) referred to as SYD985 in the present specification has an average DAR in the range of 2.6-2.9.

In one embodiment, SYD985, also known as trastuzumab vc-seco-DUBA, is an ADC of formula (II) having an average DAR of about 2.8. This SYD985 is a mixture consisting of about 65% DAR2 species, about 30% DAR4 species, and about 5% DAR6 species. The DAR2 species consist of ADCs wherein two linker drugs are conjugated to the cysteine residues of one interchain disulfide bridge between the heavy- and light chains and ADCs wherein two linker drugs are conjugated to the cysteine residues of one interchain disulfide bridge between the heavy chains. The DAR4 species consist of ADCs wherein four linker drugs are conjugated to the cysteine residues, predominantly in two isomers, in one isomer the four linker drugs are conjugated to cystein residues of the two interchain disulfide bridges between the heavy and light chains, in the other isomer the four linker drugs are conjugated to the cysteine residues of the two interchain disulfide bridges between the heavy chains. The DAR6 species consist of ADCs wherein six linker drugs are conjugated, the predominant isomer is an ADC wherein two linker drugs are conjugated to the cysteine residues of one interchain disulfide bridge between the heavy and light chains and four linker drugs are conjugated to the cysteine residues of the two interchain disulfide bridges between the heavy chains.

The compositions of the present invention additionally may comprise a bulking agent. Typical bulking agents include dextran, polyvinylpyrrolidone, serine, glycine, mannitol, inositol, sorbitol, and hydroxyethyl starch. Preferred bulking agents are mannitol and sorbitol. The most preferred bulking agent is mannitol. The bulking agent is present in an amount sufficient to decrease the lyophilization process time and/or to improve cake appearance. Preferably, no bulking agent is included in the composition in accordance with the present invention. Most preferably, the composition of the present invention consists of or consists essentially of an ADC of formula (I) or (II), a buffering agent, a lyoprotectant, and a surfactant as described herein above.

The present invention further provides a process for the lyophilization of a composition comprising an ADC of formula (I) or (II) in accordance with the present invention, the process comprising the steps of a) freezing a pre-lyophilization aqueous solution of a composition comprising an ADC of formula (I) or (II), a buffering agent, a lyoprotectant, and a surfactant wherein the molar ratio of lyoprotectant to ADC is 1,400-3,200 to 1, b) primary drying at a product temperature below the collapse temperature of the composition at a pressure below atmospheric pressure, and c) secondary drying at a product temperature above 0° C. and below the glass transition temperature of the composition at a pressure below atmospheric pressure. Preferably, the composition is frozen using a shelf temperature of −45° C. to −30° C., the primary drying is performed at a shelf temperature of −25° C. to −5° C. at a pressure below 0.2 mbar, and the secondary drying is performed at a shelf temperature of 15° C. to 40° C., 20° C. to 40° C. or 25° C. to 40° C. at a pressure below 0.2 mbar. Preferably, secondary drying is performed at a shelf temperature of about 20° C.

In an alternative embodiment, the process comprises the steps of a) freezing a pre-lyophilization aqueous solution of a composition in accordance with the present invention, b) primary drying at a product temperature below the collapse temperature of the composition at a pressure below atmospheric pressure, and c) secondary drying at a product temperature below the glass transition temperature of the composition at a pressure below atmospheric pressure, wherein the freezing step a) comprises an annealing step.

Preferably, the annealing step is performed at a shelf temperature of −25° C. to −10° C. for 0.5 to 6 hours or 1 to 6 hrs. More preferred is an annealing step at a shelf temperature of −25° C. to −15° C. for 1 to 5 hrs or 2 to 5 hrs. Even more preferred, step a) comprises lowering the shelf temperature of the apparatus at a pressure of 1,000 mbar at a rate of 0.2-1° C./min, to a shelf temperature of −50° C. to −30° C., subsequently maintaining this temperature for 30 min to 1.5 hrs, then raising the shelf temperature at a rate of 0.2-1° C./min to a shelf temperature of −25° C. to −10° C., and maintaining this temperature for 0.5 to 3 hours or 1.5 to 3 hrs, followed by cooling at a rate of 0.2-1.0° C./min to a shelf temperature of −50° C. to −40° C., followed by maintaining that temperature for 1-2 hrs.

The present inventors found that inclusion of an annealing step surprisingly decreased the lyophilisation process time drastically. When an annealing step of no more than 4 hours is included, the total process time decreases by 40 hours or more. As well, the morphology of the lyophilisate is optimal if an annealing step is included. The porosity of the cake increases, leading to faster and more homogeneous drying, and residual moisture after primary drying is low.

EXAMPLES

Preparation of Pre-Lyophilisation Solutions of SYD985

The ADC SYD 985 (i.e. trastuzumab vc-seco-DUBA) was prepared and purified according to methods and procedures published in the supplement of DOKTER, W et al. in Mol. Cancer Ther.; 13(11) November 2014, 2618-2629. After purification, the SYD985 solution was concentrated and diafiltrated using the aqueous solutions as depicted in Table 1 without surfactant using a single-use tangential flow cassette having a polyethersulfone membrane with a 30 kDa cut-off (Sius™). After diafiltration, surfactant was added and the solution was diluted to 10 mg/ml of SYD985. Then the final solution was immediately frozen and stored at −70° C. The SYD985 concentration was determined using UV-VIS and is expressed in mg/ml. Molar amounts were calculated using a molecular weight of 151.8 kDa for SYD 985 (average DAR of 2.7).

TABLE 1

Composition of pre-lyophilization solution*

|  | I Comparative | II Comparative | III | IV | V | VI Comparative |
|---|---|---|---|---|---|---|
| SYD985 | 10 mg/ml | 10 mg/ml | 10 mg/ml | 10 mg/ml | 10 mg/ml | 10 mg/ml |
| Histidine | 10 mM | 10 mM | 10 mM | 5 mM | 5 mM | 10 mM |
| Trehalose.2H$_2$O | 20 mg/ml | 30 mg/ml | 40 mg/ml | 40 mg/ml | 40 mg/ml | 82.5 mg/ml |
| Mannitol | 50 mg/ml | 0 mg/ml | 0 mg/ml | 0 mg/ml | 0 mg/ml | 0 mg/ml |
| Polysorbate 20 (m/v) | 0.01% | 0.01% | 0.01% | 0.01% | 0.01% | 0.01% |
| pH | 5.7 | 6.0 | 6.0 | 6.0 | 5.7 | 6.0 |
| Molar ratio Trehalose:SYD985 | 800:1 | 1,200:1 | 1,605:1 | 1,605:1 | 1,605:1 | 3,310:1 |

*The composition of the pre-lyophilization solution is the same as the composition of the solution obtained by reconstituting the lyophilized cake.

Lyophilization Process Used to Determine R&D Stability of Solutions I-VI

The frozen solutions I-VI were thawed at room temperature (RT) and, if free of precipitates, filtered over a 0.22 μm filter and filled into vials. The vials were loaded into a small scale freeze drying apparatus. The lyophilization was performed by lowering the shelf temperature to −35° C., followed by primary drying at 0.075 mbar at a shelf temperature of −10° C., and secondary drying at a shelf temperature of 40° C. In composition I containing mannitol, an annealing step of 4 hrs at a shelf temperature of −20° C. was introduced between the freezing and primary drying step. In composition VI having over 80 mg/ml trehalose, an annealing step at −12° C. for 5 hrs was introduced after freezing to −40° C., primary drying was performed at 0.075 mbar and −21° C., required to avoid collapse of the lyophilisate. An intermediate drying step at −5° C. was introduced between primary and secondary drying to prevent melting. The secondary drying step was performed at 20° C.

Lyophilisation Process (General Method)

The following process is a general procedure to obtain a lyophilized composition in accordance with the present invention.

For lyophilization of SYD985, a frozen solution of SYD985 (10 mg/ml) containing 5 mM histidine, 40 mg/ml trehalose dihydrate, and 0.01% (m/v) polysorbate 20 was thawed and filtered, and 20 ml vials were filled with 8.3 ml of SYD985 solution. The vials were loaded into an Epsilon 2-6D (MartinChrist) R&D freeze dry apparatus. The shelf temperature of the apparatus was lowered at a pressure of 1,000 mbar at a rate of 0.2-1° C./min to a shelf temperature of −50° C. to −30° C., subsequently maintaining this temperature for 1 to 2 hrs, then the shelf temperature was raised at a rate of 0.2-1° C./min to a temperature of −25° C. to −10° C., this temperature was maintained for 1.5 to 3 hrs. The next step was a cooling step at a rate of 0.2-1.0° C./min to a shelf temperature of −50° C. to −40° C., followed by maintaining that temperature for 1-2 hrs. Subsequently, the pressure was decreased to 0.05-0.3 mbar, and the shelf temperature was raised again at a rate of 0.2-1° C./min to −15° C. to −5° C., and that temperature was maintained for 25 to 35 hrs at a pressure of 0.05-0.3 mbar. Then the shelf temperature was raised to 20° C. to 40° C. at a rate of 5-20° C./hour, and this temperature was maintained for 1-10 hrs.

Comparative Example without Annealing Step

The frozen solution of composition V was thawed at room temperature and, if free of precipitates, filtered over a 0.22 μm filter and filled into vials. The vials were loaded into a Epsilon 2-6D (MartinChrist) R&D freeze dry apparatus. The lyophilization was performed by lowering the shelf temperature to −40° C. at a rate of 0.2-1° C./minute, followed by primary drying at 0.075 mbar at a shelf temperature of −10° C. for 50 hrs. After primary drying, the shelf temperature was raised to 40° C. at a rate of 3° C./hr and kept at that temperature for 10 hrs. Total process time was about 92 hrs.

Lyophilization Process Results

Appearance/Quality of the Lyophilized Cake

Figure 1:
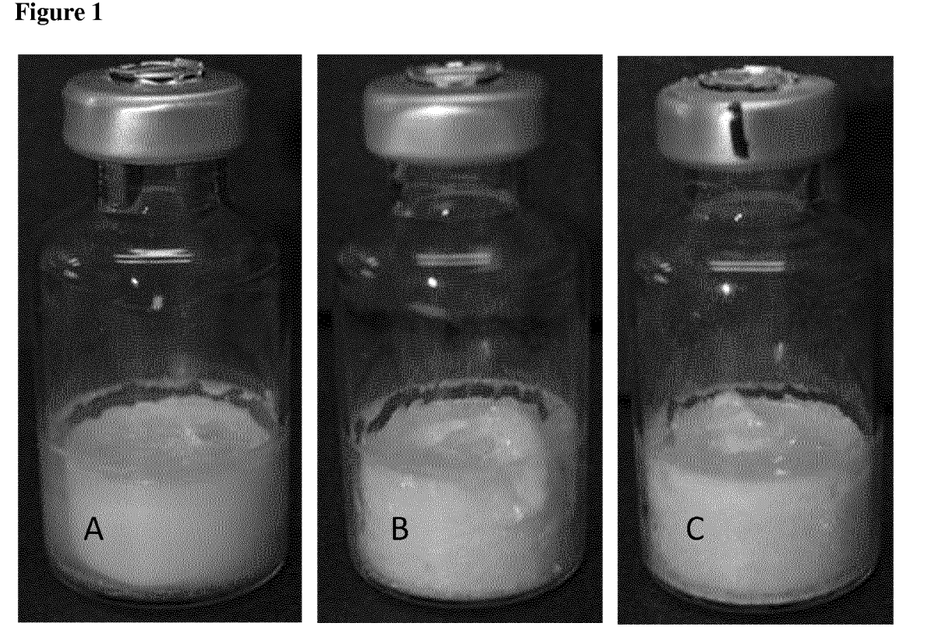
FIG. 1: Lyophilized cakes of A: placebo solution with 30 mg/ml trehalose dihydrate (similar to composition II, but without SYD985), B: composition II with 30 mg/ml trehalose dihydrate, C: composition III with 40 mg/ml trehalose dihydrate

The appearance of the lyophilized cakes of the various formulations is summarized in Table 4, row 3. Formulations I, III, IV and V of Table 1 had a good appearance after lyophilization. An amount of lyoprotectant of less than 1,400 times the molar amount of ADC gives unsatisfactorily results for the final lyophilized product, except in the presence of a considerable amount of mannitol (Formulation I). Lyophilisation of solution II resulted in a lyophilized cake of inferior quality (see FIG. 1B). Upon visual inspection, cracks and crumbles were visible. The inferior cake quality was not expected as a similar solution, without SYD985, the placebo, had a acceptable cake appearance as lyophilisate (see FIG. 1A). Lyophilization of solutions III, IV and V of Table 1 with a trehalose molar excess of 1,605 results in a cake of the desired quality (cake of solution III is shown in FIG. 1C).

Duration of the Lyophilization Process

The duration for the various lyophilization processes is summarized in Table 2.

TABLE 2

Summary Lyophilization time

|  | I | II | IV | V | VI |
|---|---|---|---|---|---|
|  | R&D process | | | | |
| no annealing | ~92 hrs | ~92 hrs | ~92 hrs | ~92 hrs | ~138 hrs |
| with annealing | ND | ND | ND | ~44 hrs | ~122 hrs |
|  | Scale-up process | | | | |
| no annealing | ND | ND | ND | ND | ~13 days* |
| with annealing | ND | ND | ND | ~63 hrs | ~8 days |

ND = not determined
*cake collapsed

The R&D lyophilization process for solution VI of Table 1 required at least 5 days (about 122 hrs), with an annealing step at −12° C. for 5 hrs, whereas lyophilization of solutions I, II, IV and V took less than 4 days (about 92 hrs without annealing).

Figure 4:
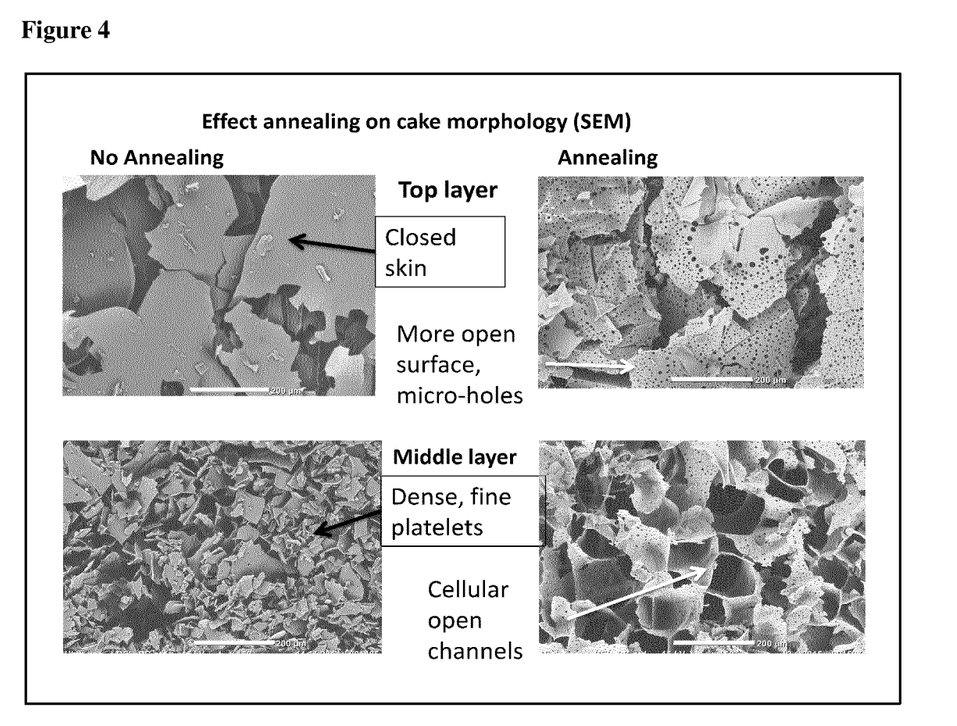
FIG. 4: SEM pictures of the top and middle layers of lyophilized cakes of composition V without annealing (left) and with annealing (right), white bar is 200 μm

The lyophilization process with annealing step has a total process time of about 44 hrs for formulation V. FIG. 4 shows a SEM picture of a lyophilized cake of solution V obtained by the comparative process which is without an annealing step (left) and a picture of a lyophilized cake with annealing (right). The porosity of the cake is clearly increased. Scale-up of solution V resulted in a process having a process time of about 63 hours.

Scale-up of solution VI to a commercial lyophilization process was unsuccessful, as the shortest commercial scale process obtained after optimization of the conditions still took over 8 days, with an annealing step. Without the annealing step the process took about 13 days and resulted in a collapsed cake. A high trehalose content in a SYD985 liquid pre-lyophilization solution is disadvantageous for the lyophilisation process.

Stability Measurements
a) Stability in Solution

The frozen solution was thawed at RT and, if free of precipitates, filtered over a 0.22 μm filter and filled into vials. Sub-visible particulate matter analysis was determined by the light obscuration technique (LO) using a PAMAS CVSS particle counter (HCB-LD-25/25 sensor, Partikelmess- and Analyse Systeme GmbH). The procedure is performed in accordance with the Ph. Eur. <2.9.19>, particulate contamination; sub-visible particles. A sample volume of 300 μl is measured (prerun volume: 0.8 mL, rinse volume: 5 mL, fill and rinse rate: 10 mL/min). At least 3 successive LO measurements were performed per sample. Results are analyzed using PMA software.

$Z_{average}$, an indication of particle size, to determine aggregation in solution, was measured using dynamic light scattering (DLS). Analysis was performed on a Zetasizer APS (Malvern Instruments, λ0=830 nm, θ=90°). A sample volume of 100 μl is measured. Per sample at least 3 successive DLS measurements were performed with 2-minutes time intervals to allow solutions to be at rest. During all measurements, temperature was kept constant at 25° C. and scattering results were compensated for viscosity.

b) Stability of the Lyophilized Compositions

Lyophilized samples were reconstituted using water for injection. All measured lyophilized compositions were easily reconstitutable.

The percentage of high molecular weight material (HMW) and monomer of SYD985 in the reconstituted compositions I, III, IV, V and VI was determined by High Performance Liquid Chromatography (HPLC) in Size Exclusion Chromatography (SEC) on a Shimadzu UFLC system with a: TSKgel G3000SWxl, 5 μm, 7.8 mm×30 cm analytical column of Joint Analytical Systems (PN 08541) at a column temperature of 25° C., using a 50 mM phosphate buffer with 300 mM NaCl of pH 7.5 as mobile phase at a flow rate of 0.3 ml/minute. Typically, 50 μl of the reconstituted formulation was diluted to a concentration of approximately 1.0 mg SYD985/mL.

Stability Results
a) Stability in Solution

Table 3 provides a summary of the stability results for the pre-lyophilization solutions of Table 1. The stability of solution II was not determined as the appearance after lyophilization was not acceptable. All five measured solutions measured showed comparable stability, except for solution I. Solution I of Table 1 with a trehalose molar excess of about 800 resulted in decreased stability in solution (see Table 3). After 1 month at RT, a protein-aceous precipitate was observed. For solution I decreased colloidal stability was observed as well with LO and DLS measurements after 1 month at room temperature (RT). Solution I has a large amount of particles >10 μm at t=1 month as observed with LO, whereas the other solutions had low amounts of particles of this size. $Z_{average}$ measured with DLS for the solutions kept for 1 month is as well significantly increased in solution I as compared to the other solutions.

TABLE 3

| | Stability in solution | | | | | |
|---|---|---|---|---|---|---|
| | I | II | III | IV | V | VI |
| Molar ratio Trehalose:SYD985 | 800:1 | 1,200:1 | 1,605:1 | 1,605:1 | 1,605:1 | 3,310:1 |
| Stability solution T = 1 m at RT | Proteinaceous precipitate | ND[1] | clear | clear | clear | clear |
| LO T = 1 m at RT | – | ND[1] | + | + | + | + |
| DLS (=1 m at RT) $Z_{average}$ (nm) | >10 | ND[1] | 3.7 | 2.9 | 3.1 | 3.8 |

[1]As the lyo cake was not of acceptable quality, no further measurements were performed.
ND is not determined
– inferior, + acceptable Both solutions IV and V with a histidine concentration of 5 mM (IV and V) have lower $Z_{average}$ values than the values measured for III and VI, having a histidine concentration of 10 mM.

b) Stability of the Lyophilized Compositions

Figure 2:
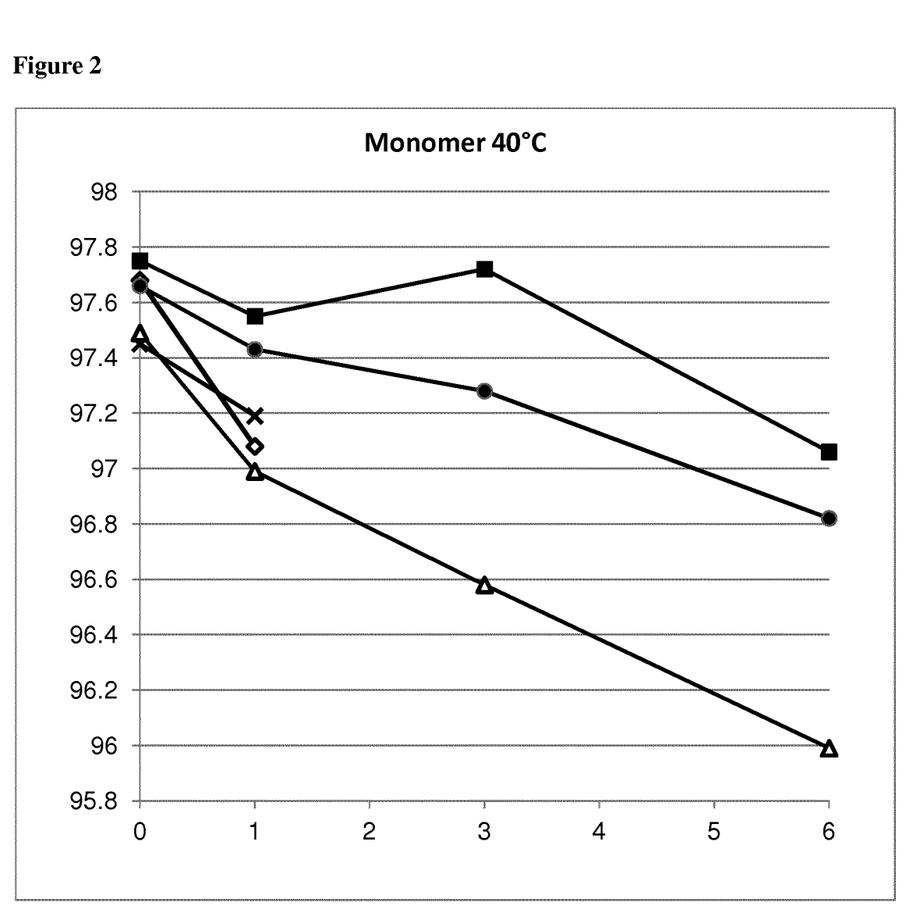
FIG. 2: Stability results: Y axis: percentage SYD985 monomer in lyophilized composition I (Δ), III (x), IV (◇), V (●), and VI (■) at 40° C., X axis: time in months
Figure 3:
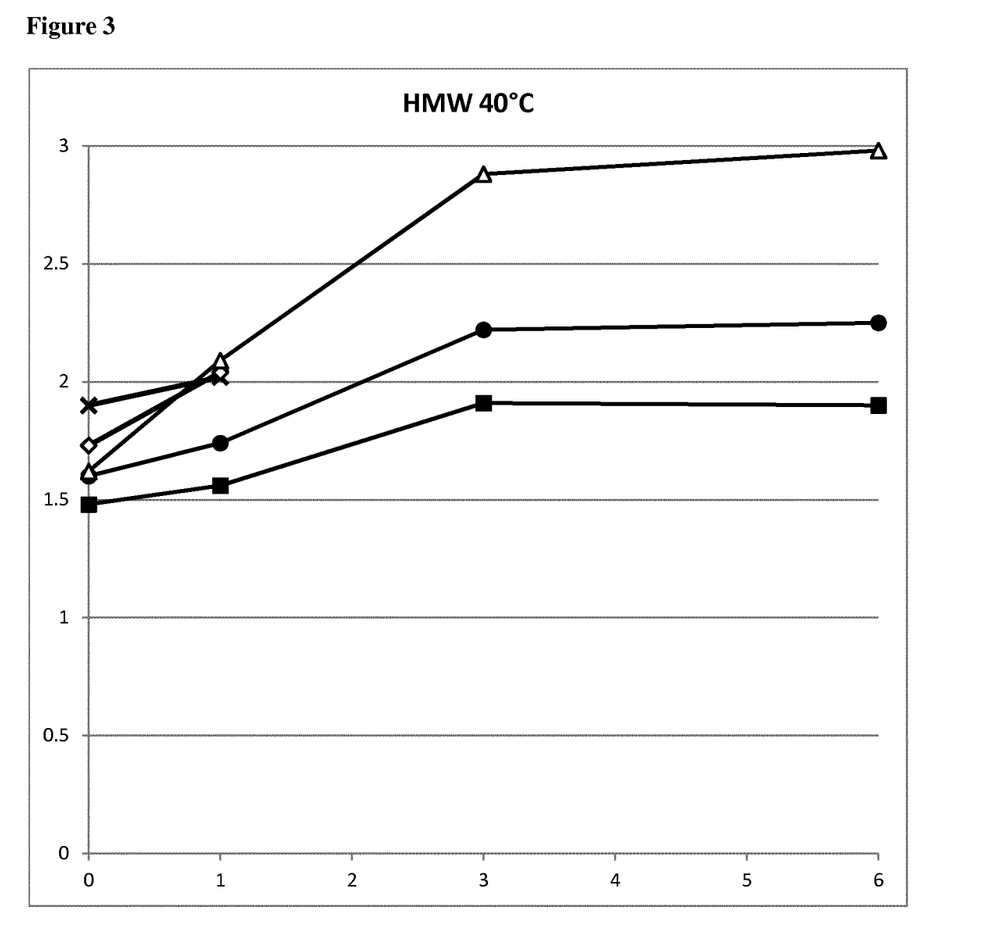
FIG. 3: Stability results: Y axis: percentage high molecular weight (HMW) particulates in lyophilized composition I (Δ), III (x), IV (◇), V (●), and VI (■) at 40° C., X axis: time in months

FIGS. 2 and 3 show that when solution I of Table 1 is lyophilized, in the lyophilized cake the % monomer decreases, whereas the % HMW increases over time at 40° C., indicative of decreased stability. FIGS. 2 and 3 show that for the formulations V and VI the decrease in % monomer as well as the increase in % HMW over time is significantly lower, as compared to formulation I. The amount of monomer in reconstituted solutions III and IV at t=1 month is higher than the amount of monomer in solution I. The amounts of HMW at t=1 month are similar for solutions I, III and IV.

TABLE 4

| Overview of lyo stability and cake quality | | | | | | |
|---|---|---|---|---|---|---|
| | I | II | III | IV | V | VI |
| Molar ratio Trehalose:SYD985 | 800:1 | 1,200:1 | 1,605:1 | 1,605:1 | 1,605:1 | 3,310:1 |
| stability in lyo cake | – | ND[1] | + | + | ++ | ++ |
| cake quality | + | – | ++ | ++ | ++ | + |
| Lyo time | + | + | + | + | + | – |

[1]Not determined because of the low quality of the lyophilisate of solution II.
– inferior, + acceptable, ++ good

The invention claimed is:

1. A lyophilized composition comprising an antibody-drug conjugate of formula (I), a buffering agent, a lyoprotectant, and a surfactant wherein the molar ratio of lyoprotectant to antibody-drug conjugate is 1,400-3,200 to 1, wherein mAb is a monoclonal antibody.

2. The composition according to claim 1 wherein the lyoprotectant is a non-reducing saccharide.

3. The composition according to claim 2, wherein the lyoprotectant is sucrose, trehalose or a mixture thereof.

4. The composition according to claim 1, wherein the buffering agent is histidine, citrate or succinate.

5. The composition according to claim 1, wherein the surfactant is an alkyl glycoside, poloxamer or polysorbate.

6. The composition according to claim 1, wherein the monoclonal antibody is an anti-HER2 antibody.

7. The composition according to claim 1, consisting essentially of an antibody-drug conjugate of formula (I), a buffering agent, a lyoprotectant, and a surfactant wherein the molar ratio of lyoprotectant to antibody-drug conjugate is 1,400-3,200 to 1.

8. The composition according to claim 1, wherein the molar ratio of lyoprotectant to antibody-drug conjugate is 1,400-2,000 to 1.

9. The composition according to claim 8, wherein the molar ratio of lyoprotectant to antibody-drug conjugate is 1,400-1,800 to 1.

10. A process for the preparation of the composition according to claim 1, comprising the steps of a) freezing a pre-lyophilization aqueous solution of a composition of claim 1, b) primary drying at a product temperature below the collapse temperature of the composition at a pressure below atmospheric pressure, and c) secondary drying at a product temperature above 0° C. and below the glass transition temperature of the composition at a pressure below atmospheric pressure.

11. The process of claim 10 wherein the freezing step a) comprises an annealing step, wherein the annealing step is performed for 0.5 to 6 hours at a shelf temperature in the range of −25° C. to −10° C.

12. A composition comprising an antibody-drug conjugate of formula (I), a buffering agent, a lyoprotectant, a surfactant, and water, wherein the molar ratio of lyoprotectant to antibody-drug conjugate is 1,400-3,200 to 1, wherein mAb is a monoclonal antibody.

13. The composition according to claim 12 wherein the lyoprotectant is a non-reducing saccharide.

14. The composition according to claim 13, wherein the lyoprotectant is sucrose, trehalose or a mixture thereof.

15. The composition according to claim 12, wherein the buffering agent is histidine, citrate or succinate.

16. The composition according to claim 12, wherein the surfactant is an alkyl glycoside, poloxamer or polysorbate.

17. The composition according to claim 12, wherein the monoclonal antibody is an anti-HER2 antibody.

18. The composition according to claim 12, consisting essentially of an antibody-drug conjugate of formula (I), a buffering agent, a lyoprotectant, and a surfactant wherein the molar ratio of lyoprotectant to antibody-drug conjugate is 1,400-3,200 to 1.

19. The composition according to claim 12, wherein the molar ratio of lyoprotectant to antibody-drug conjugate is 1,400-2,000 to 1.

20. The composition according to claim 19, wherein the molar ratio of lyoprotectant to antibody-drug conjugate is 1,400-1,800 to 1.

21. The composition according to claim 12, wherein the antibody-drug conjugate is present in a concentration of 1-30 mg/ml.

22. The composition according to claim 12, wherein the buffering agent is present in a concentration of 2.5-25 mM.

23. The composition according to claim 12, wherein the composition has a pH of 5.3-6.0.

24. The composition according to claim 12, comprising an antibody-drug conjugate of formula (II), histidine, trehalose, and polysorbate 20, wherein the molar ratio of trehalose to antibody-drug conjugate is about 1,605 to 1, and wherein the antibody-drug conjugate is present in an amount of about 10 mg/ml, the concentration of histidine is about 5 mM, the amount of polysorbate 20 is about 0.01% (mass/volume), and the pH is about 5.7.

25. The composition according to claim 24 consisting essentially of an antibody-drug conjugate of formula (II), histidine, trehalose, and polysorbate 20, wherein the molar ratio of trehalose to antibody-drug conjugate is about 1,605 to 1, and the antibody-drug conjugate is present in an amount of about 10 mg/ml, the concentration of histidine is about 5 mM, the amount of polysorbate 20 is about 0.01% (mass/volume), and the pH is about 5.7.

* * * * *

UNITED STATES PATENT AND TRADEMARK OFFICE
CERTIFICATE OF CORRECTION

PATENT NO. : 11,077,204 B2
APPLICATION NO. : 15/743413
DATED : August 3, 2021
INVENTOR(S) : Osinga et al.

Page 1 of 2

It is certified that error appears in the above-identified patent and that said Letters Patent is hereby corrected as shown below:

In the Specification

In Column 8, Lines 25-44, delete

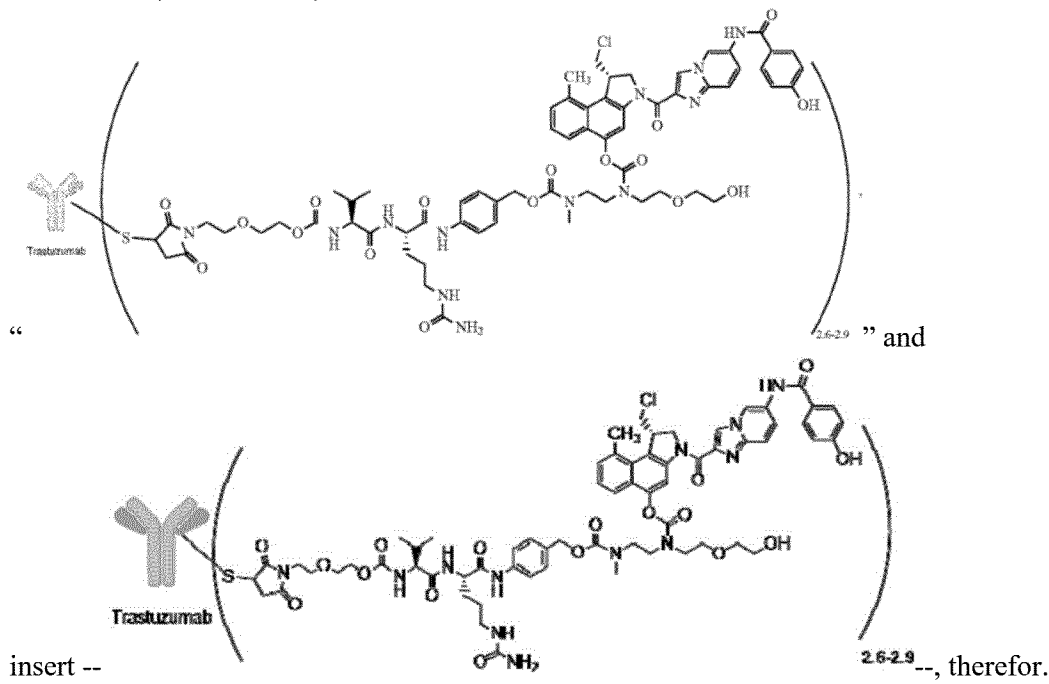

insert --

In the Claims

In Claim 2, Column 15, Line 30, delete "claim 1" and insert -- claim 1, --, therefor.

In Claim 11, Column 16, Line 40, delete "claim 10" and insert -- claim 10, --, therefor.

In Claim 13, Column 17, Line 5, delete "claim 12" and insert -- claim 12, --, therefor.

Signed and Sealed this
Twenty-third Day of November, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 11,077,204 B2

In Claim 24, Column 18, Lines 19-36, delete

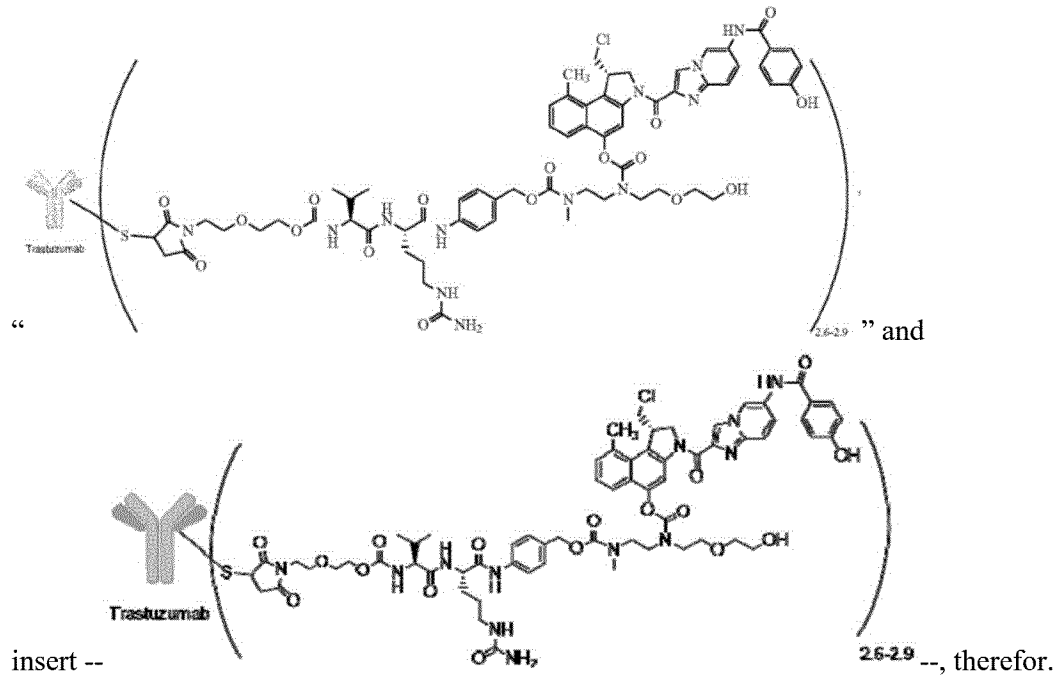

insert -- ... 2.6-2.9 --, therefor.

In Claim 25, Column 18, Line 44, delete "claim 24" and insert -- claim 24, --, therefor.